(12) United States Patent
Weiss et al.

(10) Patent No.: US 8,855,740 B1
(45) Date of Patent: Oct. 7, 2014

(54) SYSTEM AND METHOD FOR DETERMINING SIZE AND SIZE DISTRIBUTION OF MAGNETIC NANOPARTICLES USING VSM MAGNETIZATION DATA

(71) Applicant: ARkival Technology Corp., Nashua, NH (US)

(72) Inventors: Ronald D. Weiss, Nashua, NH (US); Robert Kaiser, Edmonds, WA (US)

(73) Assignee: Arkival Technology, Corp., Nashua, NH (US)

( * ) Notice: Subject to any disclaimer, the term of this patent is extended or adjusted under 35 U.S.C. 154(b) by 0 days.

(21) Appl. No.: 14/206,882

(22) Filed: Mar. 12, 2014

Related U.S. Application Data

(63) Continuation of application No. 13/734,632, filed on Jan. 4, 2013, now Pat. No. 8,700,124.

(60) Provisional application No. 61/696,544, filed on Sep. 4, 2012.

(51) Int. Cl.
| | |
|---|---|
| *A61B 5/05* | (2006.01) |
| *G01R 33/56* | (2006.01) |
| *A61B 5/055* | (2006.01) |
| *A61B 5/00* | (2006.01) |
| *A61K 49/18* | (2006.01) |

(52) U.S. Cl.
CPC ........ *G01R 33/5601* (2013.01); *G01R 33/5608* (2013.01); *A61B 5/055* (2013.01); *A61B 5/7225* (2013.01); *A61K 49/1824* (2013.01)
USPC ........... 600/410; 600/407; 600/424; 600/419; 600/420; 600/422

(58) Field of Classification Search
None
See application file for complete search history.

(56) References Cited

U.S. PATENT DOCUMENTS

| | | | |
|---|---|---|---|
| 8,486,720 B2 | 7/2013 | Banerjee et al. | |
| 8,700,124 B2 * | 4/2014 | Weiss et al. | 600/410 |
| 2011/0059550 A1 | 3/2011 | Haik | |

OTHER PUBLICATIONS

R.E. Rosensweig, et al. "Study of Ferromagnetic Liquid," Mar. 1967, Office of Advanced Research and Technology, National Aeronautics and Space Administration, Contractor Report #91684, 241 pages, see pp. 76-89 and 90-115.

* cited by examiner

*Primary Examiner* — Joel Lamprecht
(74) *Attorney, Agent, or Firm* — Preti Flaherty Beliveau & Pachios LLP

(57) ABSTRACT

A method and apparatus for performing accurate measurements of the magnetic properties of magnetic nanoparticles (MNPs) in both liquid media and biological matrices for providing information on their size, size distribution and concentration in these media and matrices and, resulting in parameters that influence their functionality and effectiveness.

15 Claims, 9 Drawing Sheets

Table 1

| Run No. | MT-1 LF | MT-2LF | MT-3 LF | MT-4LF | Bio 1 | Bio 3 |
|---|---|---|---|---|---|---|
| Material | Solid | Solid | Liquid | Liquid | MNP Infused Liver | MNP Infused Liver |
| Average $R^2$ Value (High Field) | 0.99+ | 0.99+ | 0.99+ | 0.99 | 0.99+ | 0.99 |
| $V_n$, cm3 | $(3.78\pm0.19)$E-19 | $(3.94\pm0.28)$E-19 | $(3.46\pm0.47)$E-19 | $(3.95\pm0.73)$E-19 | $(4.11\pm0.09)$E-19 | $(5.53\pm0.22)$E-19 |
| $D_n$, nm | 9.09±0.15 | 9.22±0.21 | 8.82±0.39 | 9.20±0.56 | 9.36±0.06 | 10.30±0.13 |
| $V_v$, cm3 | $(1.98\pm0.10)$E-18 | $(1.92\pm0.15)$E-18 | $(2.71\pm0.42)$E-18 | $(2.64\pm0.17)$E-18 | $(1.42\pm0.18)$E-18 | $(1.49\pm0.07)$E-18 |
| $D_v$, nm | 15.8±0.3 | 15.6±0.3 | 17.5±1.0 | 17.4±1.7 | 14.1±0.5 | 14.3±0.1 |
| Particle Diameter Diversity | 1.73±0.04 | 1.70±0.07 | 1.96±0.15 | 1.88±0.18 | 1.50±0.05 | 1.39±0.04 |
| Msat, emu/g | 39.04±0.10 | 36.53±0.12 | 5.64±0.01 | 5.63±0.03 | 0.247±0.003 | 0.285±0.001 |
| Conc Magnetic Material, vol-% | 9.76%±0.02% | 9.13%±0.03% | 1.41%±0.03% | 1.41%±0.01% | 0.06%±0.000% | 0.07%±0.000% |
| Initial Susceptibility, $\chi_o$, emu/oe-g | 0.198±0.001 | 0.179±0.002 | 0.03935±0.0008 | 0.03815±0.0004 | 0.0009±0.0000 | 0.0011 |

*FIG. 5*

SYSTEM AND METHOD FOR DETERMINING SIZE AND SIZE DISTRIBUTION OF MAGNETIC NANOPARTICLES USING VSM MAGNETIZATION DATA

RELATED APPLICATION

This application is a continuation of U.S. Non-Provisional patent application Ser. No. 13/734,632, entitled "System and Method for Determining Size & Size Distribution of Magnetic Nanoparticles using VSM Magnetization", filed on Jan. 4, 2013, which application claims the benefit under 35 U.S.C. §119(e) of U.S. Provisional Patent Application No. 61/696,544, entitled "System and Method for Determining Size & Size Distribution of Magnetic Nanoparticles using VSM Magnetization", filed on Sep. 4, 2012, each of which is herein incorporated by reference in its entirety for all purposes.

STATEMENT REGARDING FEDERALLY SPONSORED RESEARCH OR DEVELOPMENT

N/A

BACKGROUND OF THE INVENTION

Magnetic nanoparticles (MNPs) have an increasing presence in medicine for imaging and drug delivery applications. As newer, more advanced applications evolve there is a greater need for a better understanding of their intrinsic properties as well as improved measurement technology for researchers and application developers. The measurement of MNPs in a liquid, solid or biological matrix requires an understanding of particle composition and properties. In many biological-pharmaceutical applications of MNPs, the particle suspensions are custom designed to obtain specific performance in in-vivo situations and their intended role and effectiveness in most applications depend upon the composition of the magnetic core and the chemistry of the stabilizing outer layer, as well as their size, size distribution and concentration. As a result, there is a need for accurate measurements of the magnetic properties of MNPs in both liquid media and biological matrices with respect to size, size distribution and concentration in these matrices.

BRIEF SUMMARY OF THE INVENTION

An apparatus for performing accurate measurements of the magnetic properties of MNPs in both liquid media and biological matrices for providing information on their size, size distribution and concentration in these media and matrices and, resulting in parameters that influence their functionality and effectiveness.

In one embodiment, an apparatus for determining a size and size distribution of superparamagnetic nanoparticle cores in a sample includes a container to hold the sample and a magnetic measurement device configured to perform a magnetization analysis of the sample while in the container and generate magnetization data corresponding to the sample while in the container. A processor is configured to: receive the magnetization data from the magnetic measurement device; perform a linear regression analysis of the magnetization data representing an asymptotic region in each of four branches (A, B, C, D) of a plotting of $M_H$ vs. $1/H$, where $M_H$ is the measured magnetization in a magnetic field of intensity H approaching its saturation value and generate a first correlation curve of the form $M_H = \alpha/H + \beta$; calculate both a number average particle volume, $\check{V}_n$, and a saturation magnetization, $M_{sat}$, of the sample, as a function of the first correlation curve; combine low field, linear data of $M_H$ for branches A and C, and branches B and D, and obtain two plots of $M_H$ vs. H for values of H within a range from about −50 Oe to about +50 Oe; perform a linear regression analysis of the data in each branch and generate a second correlation curve of the form $M_H = \gamma H + \delta$; calculate a volume average particle volume $\tilde{V}_v$ as a function of the saturation magnetization value Msat obtained from the high field measurements, and using the value of the slope γ for the ratio of $M_H/H$; calculate a volume average spherical equivalent magnetic particle diameter $\check{D}_v$, and a number average spherical equivalent magnetic particle diameter $\check{D}_n$ as a function of $\tilde{V}_v$ and $\hat{V}_n$; and calculate a dispersity value, $\mathit{Ð}_d$, of the sample, as a function of the diameter values $\check{D}_v$ and $\check{D}_n$.

BRIEF DESCRIPTION OF THE SEVERAL VIEWS OF THE DRAWINGS

FIG. 5 is a table of numerical values obtained on representative samples;

DETAILED DESCRIPTION OF THE INVENTION

Figure 1:
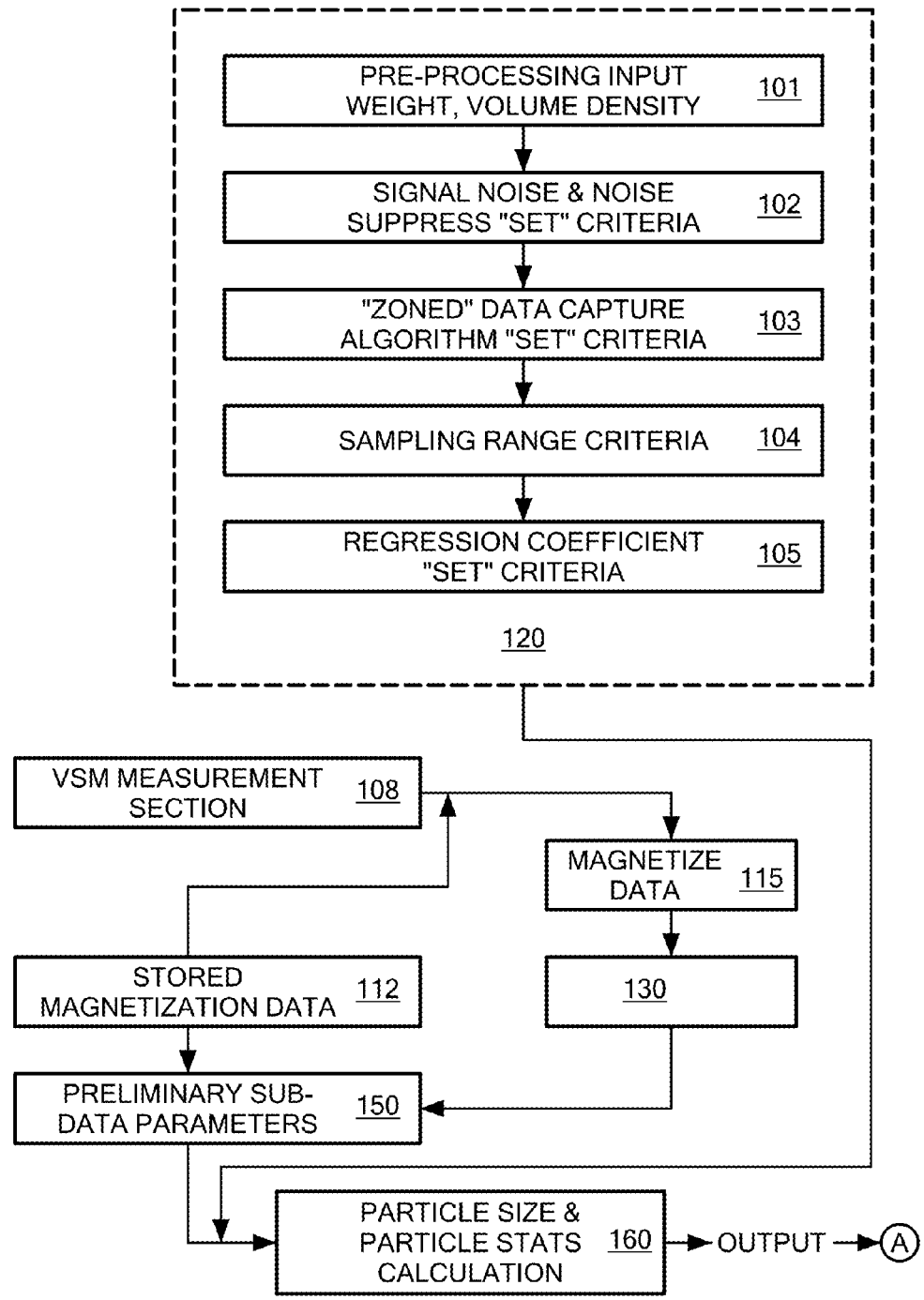
FIG. 1 is a functional block diagram of an embodiment of the present invention.

The entire contents of U.S. Non-Provisional patent application Ser. No. 13/734,632, entitled "System and Method for Determining Size & Size Distribution of Magnetic Nanoparticles using VSM Magnetization", filed on Jan. 4, 2013 and U.S. Provisional application Ser. No. 61/696,544, filed Sep. 4, 2012, entitled "System and Method for Determining Size and Size Distribution of Magnetic Nanoparticles Using VSM Magnetization," are incorporated by reference herein for all purposes.

Prior to discussion of the various embodiments of the present invention, a brief discussion of the Superparamagnetic (SPM) Theory will be provided. This is not intended to be complete as one of ordinary skill will understand and is provided in order to give background for an understanding of the description to follow.

Magnetic Nanoparticles (MNPs), in particular superparamagnetic iron oxide nanoparticles (SPIONs) as dispersions in an isotonic liquid, are a common choice for medical and other developers because of their availability and/or their in-vivo compatibility. In medical and other applications, the magnetic response of a dispersion containing SPIONs or MNPs is directly proportional to the volume concentration of magnetic material therein. Their magnetization behavior follows classical superparamagnetic (SPM) theory, according to which the magnetization $m_i$ of an isolated, isotropic single domain particle of volume $v_i$ in an applied field H can be expressed by a Langevin equation:

$$\frac{mi}{Ms} = \coth\frac{viMsH}{4\pi kT} - \frac{4\pi kT}{viMsH} \quad \text{(Eq. 1)}$$

where:
k=Boltzmann's constant,
T=absolute temperature, degrees Kelvin, and
$M_s$=domain magnetization, emu/cm$^3$ Equation 1 shows that the magnetic response of a monodisperse SPION particle system to a magnetic field is a strong function of the size of these particles.

Equation 1 can be extended to consider the magnetic properties of a suspension of particles of different sizes whereby its magnetization is obtained by considering the contribution of each size fraction in the suspension, as expressed by the following equation:

$$\frac{Mi}{\in Ms} = \sum_{i=1}^{\infty}\left(\coth\frac{viMsH}{4\pi kT} - \frac{4\pi kT}{viMsH}\right)n_iv_i \bigg/ \sum_{i=1}^{\infty} nivi \quad \text{(Eq. 2)}$$

Equation (2) describes the magnetization of superparamagnetic suspensions, assuming that the particles behave isotropically, there is no demagnetization and the domain magnetization is not a function of particle size. Equation (2) can be simplified in high and low magnetic fields to yield useful expressions on the particle size statistics of the suspension.

In high external applied fields, where $$\frac{viMsH}{4whe} \gg 1,$$

Eq. 2 can be rewritten as:

$$\frac{Mi}{\in Ms} = 1 - \left[\frac{4\pi kT}{MsH}\right]\left[\frac{\sum ni}{\sum nivi}\right] \quad \text{(Eq. 3)}$$

By definition, $$\frac{\sum nivi}{\sum ni} = \tilde{V}_n$$

the number average particle volume, and $$\frac{Mi}{\in Ms} = \frac{M}{Msat}$$

where M is the magnetization of the SPION system (in emu/cm$^3$) in a field H, and $M_{sat}$ is the magnetization of the system in an infinite field.

Thus resulting in:

$$\frac{M}{Msat} = 1 - \left[\frac{4\pi kT}{MsH\tilde{V}n}\right] \quad \text{(Eq. 4)}$$

In low external applied fields, where $$\frac{viMsH}{4\pi kT} \ll 1$$

Eq. 2 becomes:

$$\frac{M}{\in Ms} = \frac{\sum_{i=1}^{\infty}\left[\frac{1viMsH}{3*4\pi kT}nivi\right]}{\sum_{i=1}^{\infty} nivi} \quad \text{(Eq. 5)}$$

or $$\frac{M}{Msat} = \frac{1}{3}\frac{MsH}{4\pi kT}\frac{\sum nivi^2}{\sum nivi} \quad \text{(Eq. 6)}$$

Since the volume average particle volume $\tilde{V}_v$ is defined by $$\tilde{V}_V = \frac{\sum nivi^2}{\sum nivi}$$

Equation (6) becomes:

$$\frac{M}{Msat} = \frac{1}{3}\frac{MsH}{4\pi kT}\tilde{V}_v \quad \text{(Eq. 7)}$$

In summary, M is proportional to 1/H in high external applied fields and is proportional to H in low external applied fields.

Because of the relationship between the diameter and the volume of a sphere, $\tilde{V}_v$ and $\tilde{V}_n$, can also be expressed as follows:

$$\tilde{V}_v = \pi \check{D}_v{}^3/6 \quad \text{(Eq. 8) and}$$

$$\tilde{V}_n = \pi \check{D}_n{}^3/6 \quad \text{(Eq. 9)}$$

where $\check{D}_v$ and $\check{D}_n$ represent the volume average spherical equivalent magnetic particle diameter and the number average spherical equivalent magnetic particle diameter, respectively.

Since most MNP dispersions consist of non-uniform sized particles, a measure of the size dispersity of the suspensions is of practical interest because it also influences their performance and behavior. This measure, $Đ_d$, is called the particle diameter dispersity, and is defined by the IUPAC Recommendation of 2011 as the ratio of the volume average particle volume to the number average particle volume, or, for the present:

$$Đ = (\check{D}_v/\check{D}_n)^{0.33} \quad \text{(Eq. 10)}$$

In summary, from the magnetization curve of a superparamagnetic suspension with a distribution of particle sizes it is possible to calculate the number average spherical equivalent particle diameter ($\check{D}_n$) of the magnetic particles in high applied fields, volume average particle diameter ($\check{D}_v$) in low applied fields, and the particle diameter dispersity, $Ð_d$, from their ratio.

The various embodiments of the invention presented involves the material measurement process and Superparamagnetic (SPM) Theory application to evolve important information about particle sizes and their associated statistics. This description of SPM theory is not intended to be complete in every detail but is provided to give background information for an understanding of the process and methodology to obtain and report accurate particle information.

The calculations of particle size and concentration data of a system of MNPs, e.g., particulates, particulate dispersions and biological samples containing particulates, require accurate measurements of the magnetization properties as a function of the external applied field over a broad range of magnetic field intensities, from very low to very high, as discussed previously. Measurement accuracy with minimum signal noise influence is important to develop both the high field plots of M vs. 1/H and the M vs. H low field plots. This accuracy is advantageous when measuring biological sample sections containing very small quantities of very small sized MNPs exhibiting very low magnetic signal outputs.

Referring now to FIG. 1, the computer section 110 of a Vibrating Sample Magnetometer (VSM) 108 is used to obtain magnetization data 115 regarding an MNP sample measured in the VSM measurement equipment 108. The VSM 108 may be a Microsense Model 880 VSM adapted to accommodate low signal measurements. The VSM 108 includes an external applied field capability from +20,000 Oe to −20,000 Oe. The magnetization data 115 is conveyed to an internal device 130 configured to implement an embodiment of the present invention as will be described in more detail below.

It should be noted that the example system described herein uses a VSM, however, any comparable magnetic measurement device performing similar magnetic measurement functions may be used as would be understood by one of ordinary skill in the art. Accordingly, reference to a VSM herein is not intended to be limiting.

The device 110 is a computation device such as a computer having a microprocessor, such as any current microprocessor running an appropriate operating system, related memory, e.g., RAM, ROM, I/O devices including keyboard, mouse, display, etc., storage devices including hard-is drives and CD-ROMS, DVDs, etc., all connected to one another on a bus with connections to a network such as, for example, the Internet.

In the case of a low moment, i.e., a low signal output, magnetic sample, a measurement process that embodies minimum signal noise and includes technology enhancements for sensitivity accuracy and reliability is advantageous. To this end signal averaging is increased to offset measurement speed for sensitivity and accuracy. Signal averaging is a primary adjunct to increase measurement accuracy, sensitivity and repeatability. It improves noise suppression and can improve signal clarity by 10-20%. VSM measurement sensitivity however is best characterized by a quantitative analysis of related equipment noise sources and test conditions. Key variables also include sample volume and size, the sample holders, magnet gap, VSM signal pickup coils and applied field stepping conditions. These sources are all considered, some before and several during, the measurement process where different compensation approaches are introduced when required by test criteria being exercised on all measured moment data. With low moment sample signals less than 20 μemu, observed noise levels are on the order of 0.1 μemu. Field noise is on the order of ~5-15 mOe (depending on the Hall probe gain), and field resolution is ~0.001 Oe in the low field range.

A measurement process that uses a sampling algorithm optimizes 'zoned data capture' in the device 130 for improving the data quality required by the sub-data parameter processor 150. The sub-data parameters are those parameters derived from Superparamagnetic theory application such as, the number Volume $\tilde{V}_n$ and the volume average particle volume $\tilde{V}_n$ and are used to subsequently calculate particle sizes and other particle statistics. The result being a measurement process that includes software enhancements for fast and accurate data acquisition cycles, system ease-of-use for high throughput (processing) of both simple and complex magnetic measurements to produce accurate particle sizing and particle distribution statistics VSM measurements on low moment samples are also affected by the diamagnetic or paramagnetic background signal contributions arising from the diamagnetic material of which the sample holders themselves may be made, e.g., Quartz, Pyrex®, carbon fiber or other types of diamagnetic material (~50 μemu). Extracting the magnetic signals of the low moment materials from these background signals requires the sample holders' magnetic profile, and the ability of software, for subtracting this profile from the combined data. In addition, it may also be necessary to account for the presence of a matrix (e.g. a liquid such as water, either as the dispersion medium or a component of a tissue sample, a solid suspension, or the like). Accordingly, the magnetic profile of the matrix will also be subtracted from the combined data. Still further, any other material, inert or not, organic or inorganic, that will modify the background signal will be identified and subtracted. Accomplishing this is well within the capabilities of system software, and is a relatively rapid process once defined. Alternatively, magnetization data 112 that has been previously collected may be provided to the device 130. The provision of the data 112 may be via a file on a storage device collected in the pre-sample preparation stage. This could include magnetization data for signals to be subtracted as described herein.

Figure 2A:
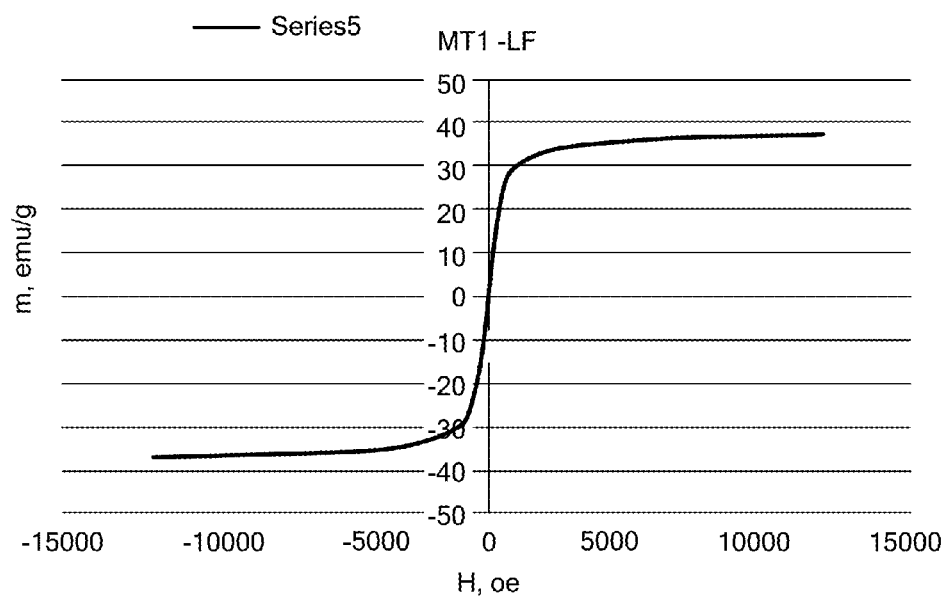
FIGS. 2A, 2B and 2C are graphical representations of processed output from an application-specific VSM adaptation for an MNP material in accordance with an embodiment of the present invention.

The VSM measurement section 108 provides the magnetization data 115 of an MNP sample that can be presented as a room temperature magnetization curve of a tarred, MNP sample placed into a sample holder of known weight and magnetic properties as generated in an external magnetic field that varies from −20,000 Oe to +20,000 Oe. When the magnetization data 115, with optional application of the functions in blocks 102, 103, 104, 105 and 112, as described below, is graphed, its shape would be similar to the one shown in FIG. 2A, commonly known as the magnetization curve.

For this application, the magnetization curve can be considered to consist of four branches:

1) Branch A—the magnetization data for increasing values of H from about 0 Oe to about +20,000 Oe;
2) Branch B—the magnetization data for decreasing values of H from about +20,000 Oe to about 0 Oe;
3) Branch C—the magnetization data for decreasing values of H from about 0 Oe to about −20,000 Oe; and
4) Branch D—the magnetization data for increasing values of H from about −20,000 Oe to about 0 Oe.

As will be described in more detail below, the high field (approaching +/−20,000 Oe) and low field branch data (approaching 0 Oe) are then used to calculate the saturation magnetization, the number average magnetic particle volume, the volume average magnetic particle volume, the spherical equivalent particle diameters, and the magnetic particle diameter dispersity.

Figure 2B:
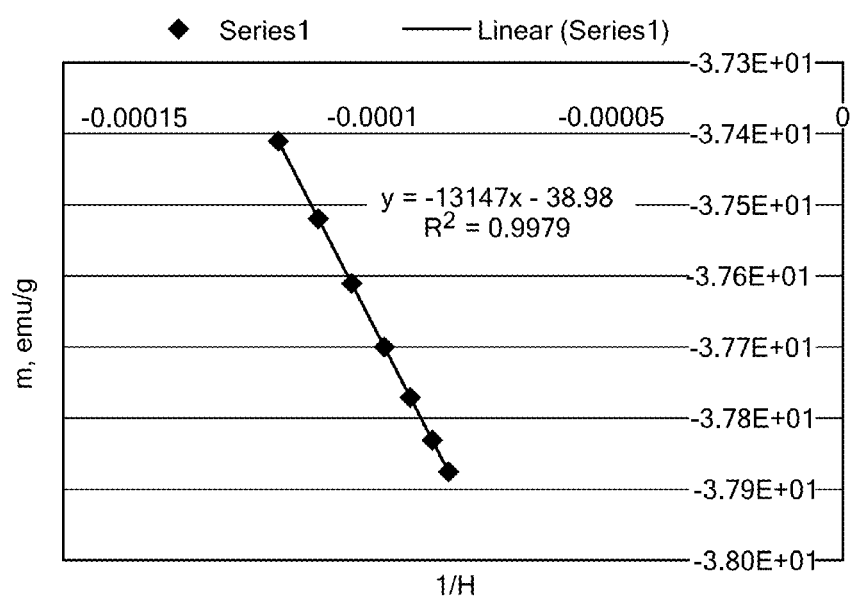
Figure 3:
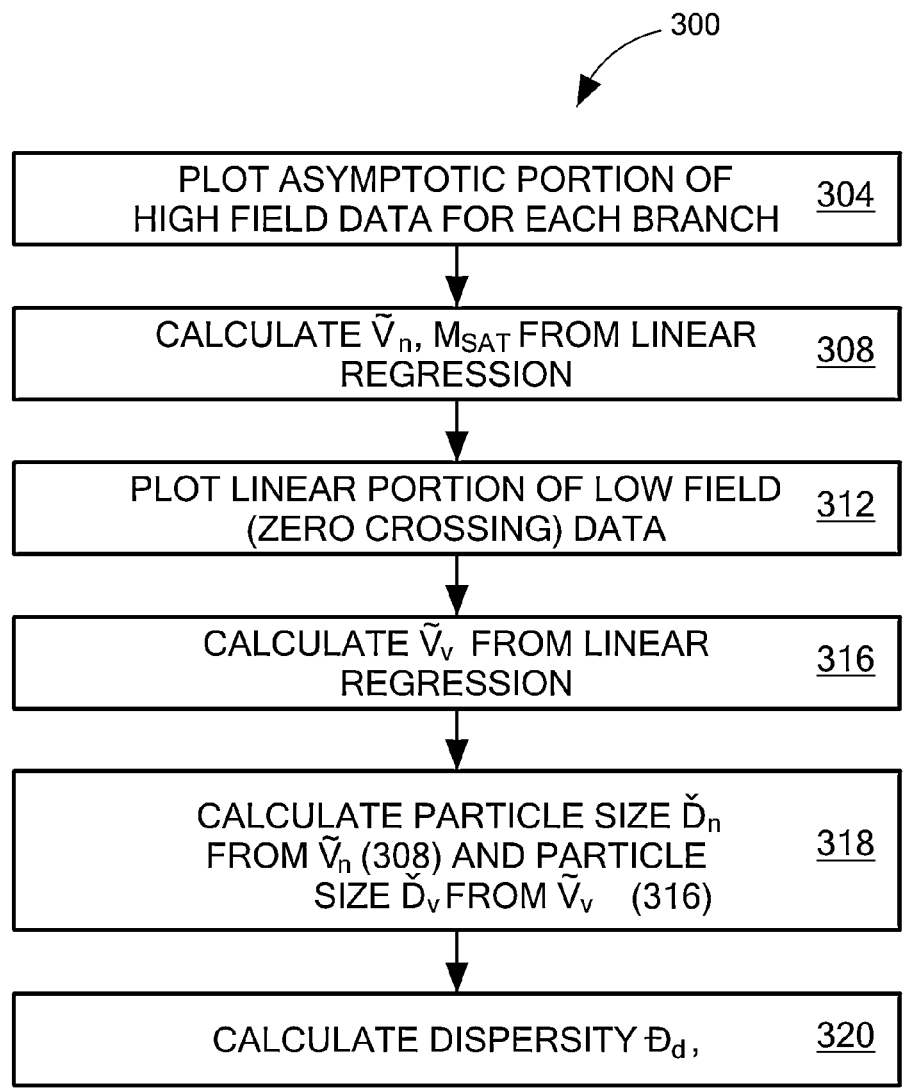
FIG. 3 is a flowchart of a method in accordance with an embodiment of the present invention.

Referring now to FIG. 3, a method 300 in accordance with an embodiment of the present invention includes, step 304, plotting the asymptotic portion of high field data for each of the four branches (A,B,C,D) as $M_H$ vs. 1/H, where $M_H$ is the measured magnetization in a magnetic field of intensity H approaching its saturation value (>10,000 Oe). The data in each branch are subjected to a linear regression analysis to generate a correlation curve of the form $M_H=\alpha/H+\beta$ as shown in FIG. 2B.

Figure 2C:
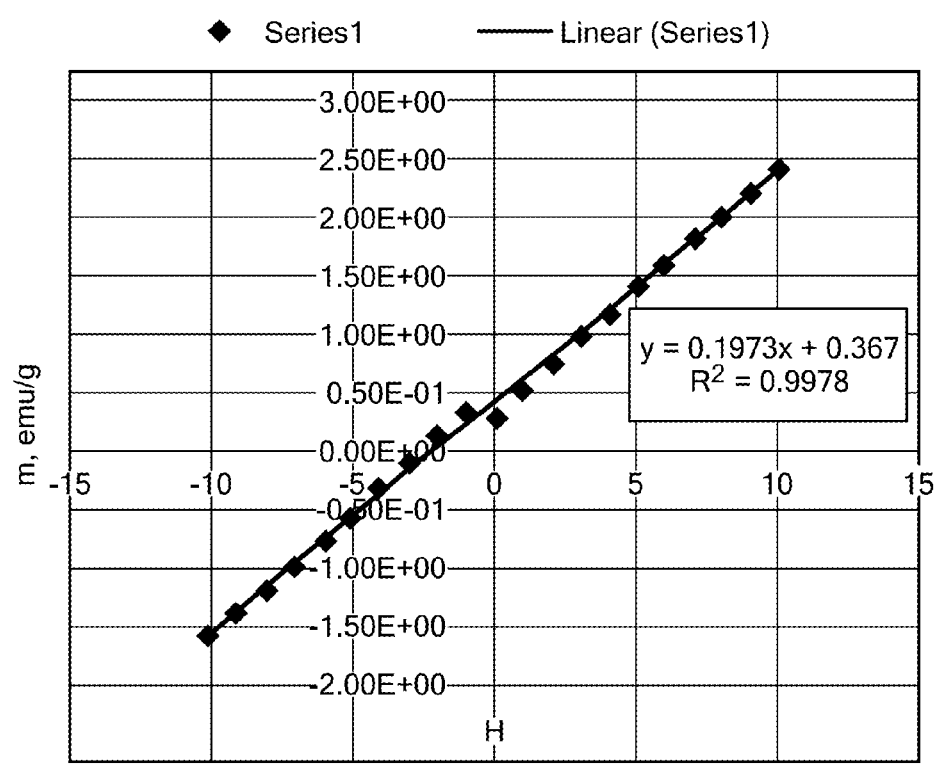

Similarly, in the method 300 in accordance with an embodiment of the present invention includes, step 312, plotting the linear portion of low field data for each of the branches (A,B,C,D) as $M_H$ vs. H, where $M_H$ is the measured magnetization in a magnetic field of intensity H approaching its zero-crossing (0 Oe) as shown in FIG. 2C.

Referring to Equation 4, this correlation provides the information needed to calculate both the number average particle volume, $\tilde{V}_n$, and the saturation magnetization, $M_{sat}$, of the sample 308. The number average particle volume, $\tilde{V}_n$, is the only unknown in the expression of the slope, $\alpha$. The saturation magnetization $M_{sat}$, by definition, is the magnetization of the sample in an infinite field, and is thus equal to the value of $M_H$, or $\beta$, when the regression line meets the y axis where $1/H=0$ $Oe^{-1}$. The average of the values $\alpha$ and $\beta$ obtained for each branch are used to obtain the reported values of $\tilde{V}_n$ and $M_{sat}$ for those data sets that have a Regression Coefficient ($R^2$) value larger than a pre-determined value, e.g., 0.95.

The low field, linear data of $M_H$ for branches A and C, and branches B and D, are combined to obtain two plots of $M_H$ vs. H for values of H within a range from about −50 Oe to about +50 Oe, more specifically, from about −10 Oe to about +10 Oe, step 312. The data in each branch were subjected to a linear regression analysis to generate a correlation curve of the form $M_H=\gamma H+\delta$. The slope $\gamma$ is, by definition, the initial susceptibility of the sample. The offset $\delta$, which is numerically small, is due to a small experimental zero off-set error that has no physical meaning, and can be disregarded. Referring to Equation 7, after substitution of the value of $M_{sat}$ obtained from the high field measurements, and using the value of $\gamma$ for the ratio of $M_H/H$, this correlation provides the information needed to calculate the volume average particle volume, $\tilde{V}_v$, 316. The average of the values $\gamma$ obtained for the two plots is used to obtain the reported values of the initial susceptibility, $\chi_o$, and of $\tilde{V}_v$, for those data sets that had a Regression Coefficient ($R^2$) value larger than a predetermined value, e.g., 0.95.

The dispersity, $Đ_d$, of the sample is then calculated by inserting the derived values of $\tilde{D}_v$ and $\tilde{D}_n$ into Equation 10, 320.

The foregoing method 300 may run on the device 110 using software written in a programming language that allows for the manipulation of the data as described above. The program may be stored in a memory that is coupled to the processor described above. This program may include a customized spreadsheet running in a program, such as Excel, as available from Microsoft Corporation, or any similar program or tool that allows for data manipulation and calculation.

As described herein, it is possible to accurately measure the size and size distribution and concentration of MNPs or SPIONs in biological matrices, as well as in liquid and solid dispersions using room temperature measurements with a VSM in conjunction with classical superparamagnetic theory, i.e., the Langevin equation.

In one embodiment of the present invention, a VSM measurement process includes a measurement algorithm to utilize classical statistical mechanics to accurately report embodied core particle sizes and particle statistics. This is done via a software module within the VSM computer system as shown in FIG. 1, that includes a series of data inputs 101 and user inputs 102-105 for the calculation 120 and operations, that is, the processing of sample measurements, including the removal of stored measurements for magnetic noise and other contributions such as, but not limited to, liquid and sample carriers/holders and noise contributions 112. The data output is the compensated magnetization data 115 collected from the sample. The compensated magnetization data 115 is then acted upon by the computerized employment of the classical statistical mechanic elements 130 as detailed in FIG. 3.

Figure 4:
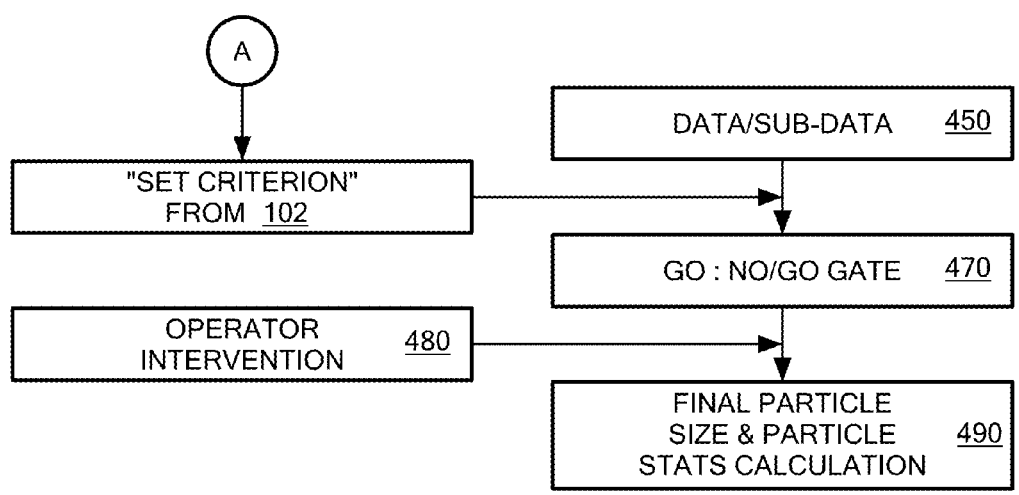
FIG. 4 is a flow chart of the real-time data processing to a user "set" of criteria designed to establish accurate, reliable and repeatable particle size and particle statistics from sub-data parameters in accordance with an embodiment of the present invention.

The resulting data output reports preliminary sub-data parameter reporting 450 that is compared with the set input criteria 102-105 whereby an operator/computer decision or intervention 480 is reached on a 'go'/'no-go' decision 470 as shown in FIG. 4. The 'no-go' decision 470 requires a change or acceptance of the user "set" criteria in step 120 for acceptance or further processing. All 'go' decisions result in the final data calculation and reporting steps 160, 490 of particle size and particle statistics.

In another embodiment of the present invention, a method of measuring particle sizes in the 1-100 nanometer size ranges allows for new pharmacological, medical & commercial applications.

The particle size measurement method for the 1-100 nanometer size range and its size reporting accuracy is completed by use of the superparamagnetic theory calculation algorithm FIG. 3; the user "set" criteria input for the minimum allowable regression coefficient 105 and the user "set" criteria of the maximum allowable signal noise 102. The user input selections can be either pre-determined default values or those adjusted to provide data acceptable to an application requirement.

In another embodiment of the present invention, a measurement method utilizes high energy magnetic fields comparable to the magnetic fields used in modern MRI technology for imaging applications, 2-10 Tesla.

The magnetic fields used for testing the magnetic materials as solids, liquids or contained in different matrices, including biological matrices, are determined and adjusted for use by the magnet gap spacing, sample size, sample holder/container size. Sample size and sample holder/container sizes can be changed in accordance with MRI or other imaging application requirements as several holder/container material options exist or can be fabricated as needed; each requiring a magnetization determination 112 as described. The magnet gap control is contained within the customary workings of the VSM and can be manually, or automatically, adjusted by the VSM operator prior to the measurements.

In another embodiment of the present invention, a measurement process measures magnetic materials within their native medium and requires no exhaustive, expensive and time-consuming preparation(s) for measurement.

The measurement of magnetic liquids or magnetic materials contained in different matrices, including biological matrices, is new to VSM measurements. A process has been developed to encapsulate the magnetic liquids, matrices containing magnet particles, and biological samples containing magnetic materials in a quartz/plastic holder for VSM measurement. The measurement process uses the pre-sampling magnetization profile of the sample holder(s) 112, an accurate sample weight measurement 101 and an air-tight sealing of contained sample within the holder. The process may also require the pre-sampling magnetization profiling of the different matrices (including biological matrices) used for the magnetic material containment 112. In another embodiment, the sample may be placed in a holder that is not air-tight.

These magnetic profiles of the sample holders and matrices are added to, or subtracted from, the sample measurements 108 and result in the "magnetization data" 115 necessary for subsequent processing.

The entire encapsulation and magnetization data collection can be completed within minutes and at relatively low cost when compared to alternative measurement methods and their required preparation—few if any provides measurement in their liquid or biological medium.

In another embodiment of the present invention, a magnetic measurement process reports magnetic core particle size and distribution measurements in a relatively simple and fast (on the order of minutes) manner and requires minimal sample preparation.

The sample preparation process for particle size and size distribution, as described above, is considerably faster than that employed by other measurement approaches (minutes compared to days). Further, the particle size data offered by most alternative technologies cannot provide the accuracy delivered by this VSM method where $10^{6-20}$ particles can be measured in a single measurement without a costly and out of carrier matrix. This measurement process embodies populations of magnetic nanoparticles ($\sim 10^{15}$) that are many orders of magnitude higher than those present in traditional electron microscope studies ($\sim 10^2$ or $10^3$ particles).

The measurement process is performed by utilizing noise suppression, has greater accuracy and repeatability and is faster due to the use of zoned data acquisition.

In another embodiment of the present invention, a measurement process can accommodate many types of materials, materials with very low magnetic signal outputs, and materials available only in very small sample sizes and weights.

The measurement of particle sizes and particle statistics from very low magnetic signal outputs, and materials available only in very small sample sizes and weights is done using the measurement technology now described. These low signal measurements include utilization of the following processes:

a) Minimizing signal noise from all sources via noise suppression that includes pick-up coil cooling (for elimination of Johnson (thermal) noise), noise bandwidth filtration, minimizing stray magnetic and electrostatic signal with input power filtration and regulation, local conductive flooring provision, localized EMF zoned-screen cages, mu-metal component shielding 102.

b) Electronic Signal smoothing, increased stepping-cycle timing, larger data collection (Sampling rates) with signal averaging 104.

c) Exacting subtractions of sample and carrier media magnetization data.

d) Establishing data acceptance with regression coefficients ($R^2$) greater than a pre-established value 105.

In another embodiment of the present invention, a measurement process uses a sampling algorithm for focused 'zoned data capture' for improving the data quality and more rapid data processing. This measurement process includes software enhancements for fast data acquisition cycles, and system ease-of-use for high throughput (processing) of both simple and complex magnetic measurements.

The measurement process uses a test algorithm that includes rapid magnetic testing by zoned data capture to produce accurate particle sizing and distribution statistics 103. The method uses an algorithm that samples magnetic data at four (4) regions of the magnetization curve: Asymptotic regions/zones approaching magnetic saturation of the material (both positive and negative applied maximum fields); Linear regions/zones approaching a zero-crossing (from both positive field application to negative field application). In each of the defined zones/regions, improved accuracy and data quality is accomplished with stepped data acquisition done with both an increased number of applied field steps as well as increased data collection time in each step. As a non-limiting example, the increased number of field steps may be 1-20 Oe/step as compared to a conventional per step range of 50-100 Oe/step with a sampling rate on the order of about 100 samples/step.

In another embodiment of the present invention, a measurement process embodies minimum signal noise and includes technology enhancements for sensitivity and reliability.

The process is performed using real-time data where the noise floor is less than 1-2% of the signal level 102 and establishing data acceptance with regression coefficients ($R^2$) greater than 0.95 105. It utilizes a measurement algorithm that includes a real-time analysis of equipment and sample noise during test. Noise sampling includes consideration for sample volume and size, sample holders, magnet gaps, signal pickup coils and field stepping conditions.

In another embodiment of the present invention, a measurement process includes a testing algorithm utilizing signal averaging to increase measurement accuracy, sensitivity and repeatability.

Using real time input data processed to user "set criteria" values 170 presents accurate sub-data parameters 150 for the calculation and reporting of particle sizes and particle statistics that have good sensitivity and accuracy and insure repeatability.

In another embodiment of the present invention, a measurement process includes variable data averaging of collected data.

Data is collected in the varying times established for each pre-determined magnetic field step done during the magnetic measurement. By applying data averaging in the zoned data regions defined in the embodiment of this disclosure, noise suppression is maximized and signal clarity results can be improved 10-20%.

In another embodiment of the present invention, a measurement process includes an algorithm that extracts the magnetic signals and noise contributions of low moment materials from their carrier materials.

By using process, software and hardware described herein, the software process 130 accomplishes the subtraction of carrier materials and sample holder magnetic profiles from the combined data from encapsulated samples with low moments. The background signals can have diamagnetic or paramagnetic background signal contributions that arise from sample holders, carrier materials and 'non-magnetic' support media ($\sim$10-50 µemu) that are subtracted from the combined data-thereby allowing sample moment measurements in the low µemu range.

In another embodiment of the present application, the determination of the size and size distribution and concentration of MNPs in biological matrices can be used to characterize MRI data taken of tumor vasculature in patients. This is done via a series of MNP Tracer solutions/particles of different but tightly controlled sizes being introduced to the tumor in sequence with accompanying MRI captures. Such studies will demonstrate the ability to match physical dimensions of therapeutic agent molecules and nanoparticles to that of tumor vascular geometry, and also provide via a minimally-invasive diagnostic procedure (MRI) an adjunct to, or a replacement of a tumor biopsy; providing also, a guide to tumor specific, therapeutic drug delivery.

In this embodiment of the present application, a biological sample containing MNPs is analyzed in accordance with the foregoing teachings and the distribution density (by particle size) of the MNPs present is determined. The relationship and correlation previously established between the VSM's findings and the corresponding MRI tumor study images (both with MNP present) will allow an MRI study alone to be the determining factor for tumor vasculature description.

In addition, a solution series of closely-sized (CS) MNP Tracers of varied and tightly controlled particle sized groupings of MNP's (in dispersions) can be used for a 'fingerprint identification' of the varied vasculature within a given tumor sample based on the average size and size dispersity of the MNP. An MRI tumor imaging series (done in coordination with the introduction of an MNP Tracer series) taken and correspondingly stored, for example, in a database. This analysis and correspondence, that is, the MRI image and the dispersity analysis is then performed for a plurality of different biological samples with different sizes, amounts, types, etc., of MNPs present, in order to establish a library of MRI images with corresponding size and dispersity within their tumor vasculatures. The image library, therefore, becomes a source for tumor fingerprinting, identification and future tumor treatment.

In one application, an MRI of a tumor is obtained with one or more MNP Tracers. The MRI image is then compared to the library of MRI images to determine if there is a visual match, as determined by a radiologist or by an automated MNP analysis program. Thus, the physician will have information as to the shape, type and progression of the tumor without the need for an invasive biopsy.

In another embodiment of the present application, the determination of the size and size distribution and concentration of MNPs in biological matrices can be used to provide custom-designed CS-MNP platforms for specific therapeutic attachments and/or drug delivery applications, a method/software/service to establish MNP particulates and their spatial distribution within a tumor and/or a method of characterizing a tumor's unique vascular architecture, CS-MNP standards (certified for both core and hydrodynamic sizes) for use and/or development of therapeutic drug delivery systems.

APPENDIX

Experiments were carried out with Ferrotec EMG 607 solution; from Ferrotec (USA) Corp., Bedford, N.H., which is a general application, medically-classified, magnetic nanoparticle suspension used as an experimental material where rapid evaporation or water miscibility is required. The manufacturer's specifications report a nominal particle diameter of 10 nm, a magnetic concentration of 2 vol-percent, a saturation magnetization of 7.96 emu/g, and an initial susceptibility of 0.123 emu/g/oe.

Measurements were performed on the as-received liquid dispersion (~0.5 cm$^3$), and on the residue of the liquid dispersion concentrated by evaporation in the VSM sample holder, and on biological specimens (chicken livers) injected with the liquid dispersion. A small section of the ferrofluid-injected matrix was cut (biopsied) and inserted in a VSM sample holder. These samples were measured in the same manner as all the other samples examined in the study.

Results

The numerical values of the duplicate experimental samples performed are summarized in Table 1 shown in FIG. 5.

Tests MT-1 LF and MT-2 LF were performed with the solid residue left after the evaporation of volatiles (water) from Ferrotec EMG 607. Runs MT-3LF and MT-4 LF were performed with the as-received Ferrotec EMG 607 dispersion. Runs Bio 1 and Bio 3 were performed with samples of Ferrotec EMG 607 infused chicken liver.

Figure 6:
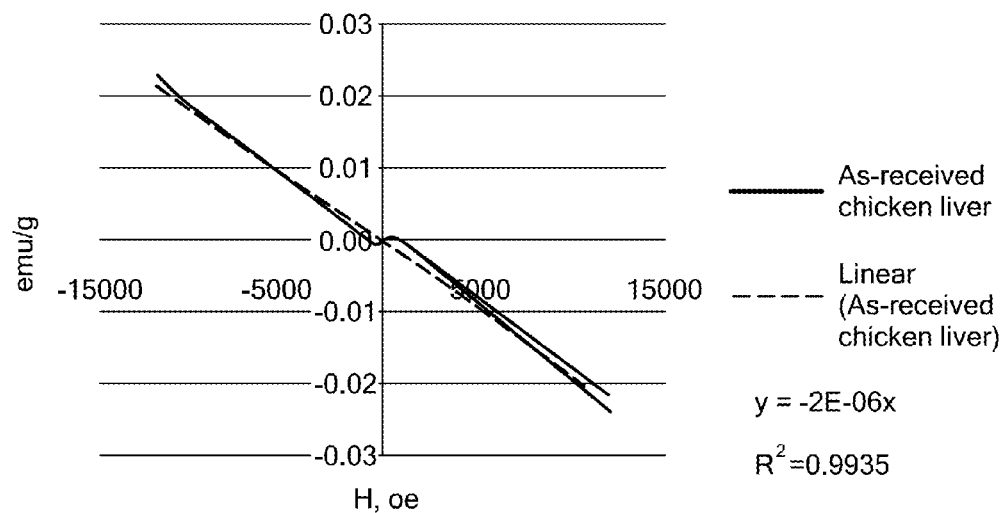
FIG. 6 is a graph showing a magnetization curve of a biological sample, as received.
Figure 7:
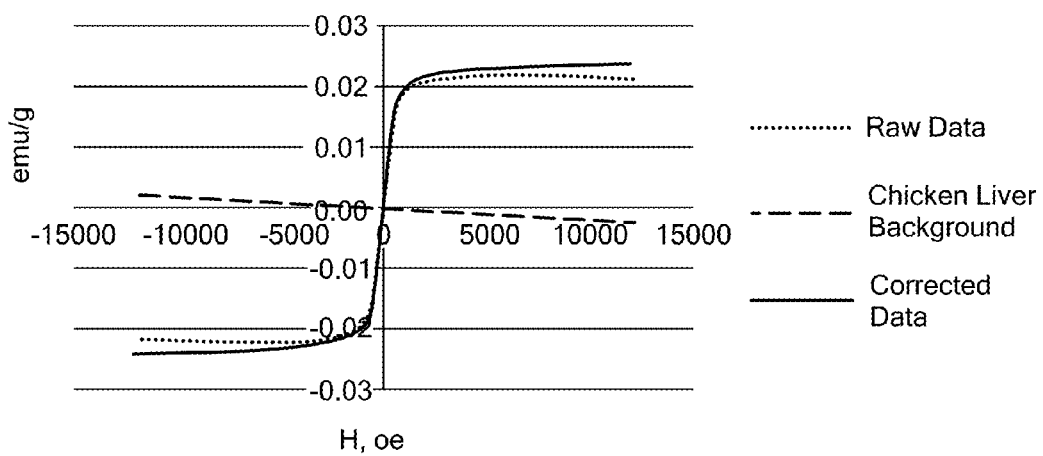
FIG. 7 is a graph showing a magnetization curve of a biological sample infused with a diamagnetic material.

Not listed in Table 1 is test Bio 2 which was performed with a sample of untreated, as-received chicken liver. This material was found to be diamagnetic, as shown by the graph of the magnetization curve of the as-received biological sample test Bio 2 shown in FIG. 6. These diamagnetic effects were a significant contributor to the magnetic signature of Ferrotech EMG 607 infused chicken liver sample, as shown by the graph of the magnetization curve of the treated biological sample test Bio 1 shown in FIG. 7. The data presented for Bio 1 in Table 1 are based on the diamagnetic corrected data curve, as are the results for Bio 3. For Bio 1 and Bio 2, the corrected magnetization in an applied field H is the sum of the measured sample value and the negative magnetization of the chicken liver sample in the same field.

Figure 8:
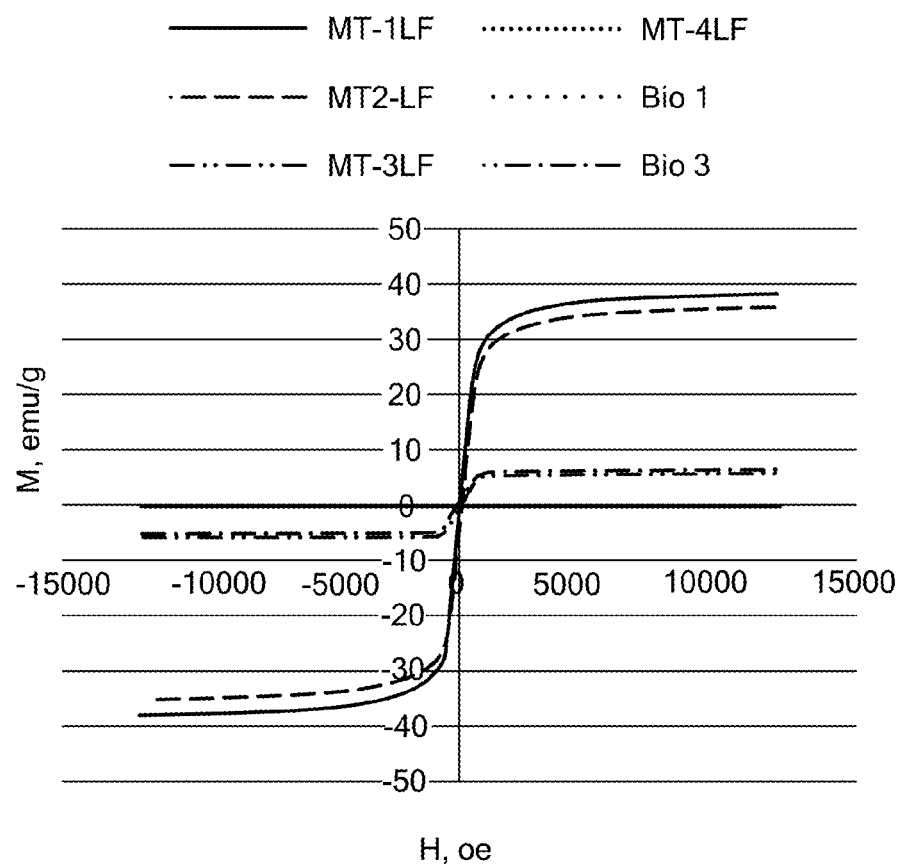
FIG. 8 is a graph of magnetization curves for the samples shown in the table in FIG. 5.

The magnetization curves, M vs. H, for the six tests listed in Table 1 of FIG. 5 are presented in FIG. 8, which is a plot of the specific magnetization of the samples (in emu/g) versus applied field. The data form three sets of curves. The first set is for the solid samples which have the highest concentration of magnetic material; the second set is for the liquid dispersions, and the third set is for the chicken liver samples which have a low concentration of magnetic particles.

The magnetization curves, M vs. H, for the tests listed in Table 1 of FIG. 5 are presented in FIG. 8 and clearly demonstrate that Ferrotec EMG 607 is a superparamagnetic material, as are the concentrates obtained by evaporation of the carrier liquid and the infused chicken liver data. The experimentally derived values of the saturation magnetization, Msat, of the various samples ranged by more than two orders of magnitude, from 0.25 emu/g to 39 emu/g. This corresponds to a range in magnetic particle concentration (obtained as the ratio of the saturation magnetization of the suspension, $M_{sat}$, to the domain magnetization of the constituting magnetic material, $M_s$) from 0.06 vol-% for the chicken liver samples to 9.6 vol-% for the concentrates. The experimentally derived values of the initial susceptibility ($\chi i$), of the various samples examined ranged from 0.0006 emu/g-Oe to 0.073 emu/g/-Oe also reflecting on the differences in MNP concentration in the various samples. The differences in particle concentration are reflected in the three sets of curves present in FIG. 8, one set for the solid concentrates, a second for the liquid dispersion, and the third for the infused chicken livers. For all samples, there results were reproducible, as can be noted from the data presented in Table 1.

The curves for the six samples presented in FIG. 8 essentially overlap, and are nearly indistinguishable, when they are plotted as the reduced magnetization, $M/M_{sat}$, versus the applied field, H, indicating a high level of similarity in the size distribution of the MNP in these dispersions.

Magnetic Particle Size Distribution

The particle size measurements of the two Ferrotec EMG 607 samples, MT-3 LF and MT-4 LF, were statistically comparable, for both the number average and volume average values. The particle size measurements of the two concentrated samples, MT-1 LF and MT-2 LF, were statistically indistinguishable for the number average values, and slightly lower for the volume average values. The differences in the values of the volume average and number average particle diameter, and as a consequence, of the dispersitivities, are a clear indication that the MNP in EMG 607 has a broad particle size distribution. The reported values of the particle dispersion are close to 2, or twice the value one would expect for monodisperse suspensions. Because of these relatively high levels of dispersity, the 20% differences between the dispersitivities of the initial and concentrated dispersions can be accounted for by experimental error. A slight difference in particle size distribution was noted for the Ferrotec EMG 607 infused chicken liver samples. It was noted that the volume average particle volume and volume average particle diameter for the infused samples were respectively 28% and 10% lower than for the other samples examined, especially the as received samples, as was, by consequence, the dispersitivity.

Comparison of Magnetic Particle Size Measurements

Figure 9:
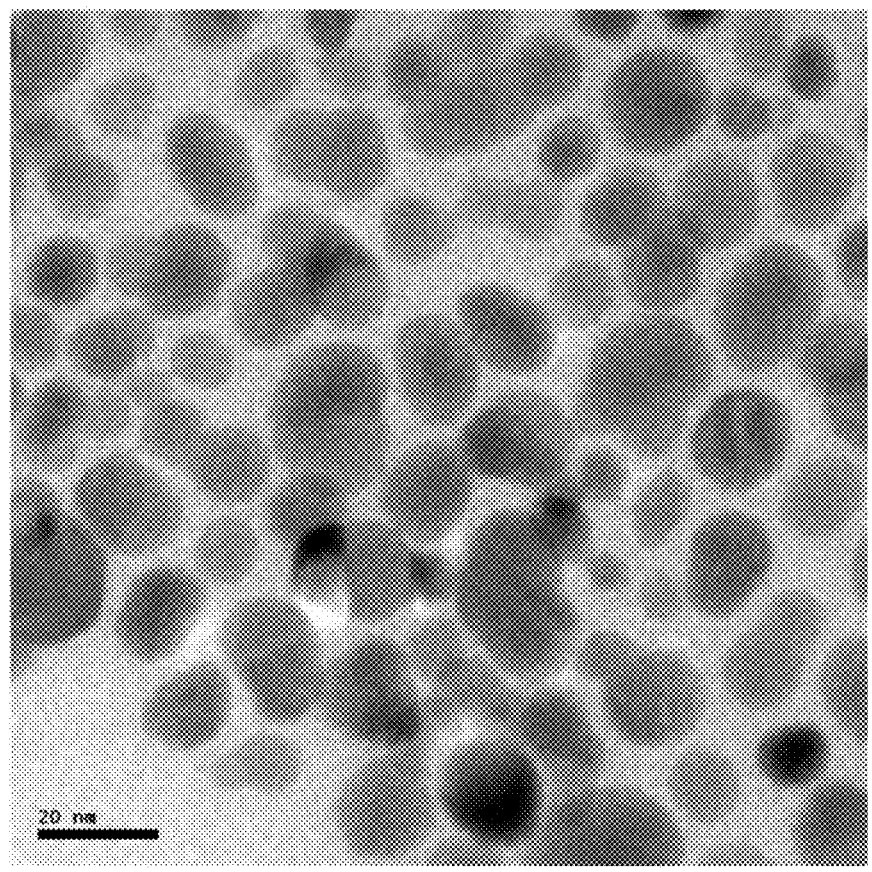
FIG. 9 is a transmission-electron photomicrograph of a magnetic suspension.

The magnetic particle measurements discussed herein address the diameter of the magnetic core of the particles in an MNP suspension. This is one of several metrics that can be, and are used to describe the size of an MNP. The reported particle diameter depends on the method of MNP measurement used. In particular, it is important to distinguish between the hydrodynamic particle diameter and magnetic core diameter. The hydrodynamic diameter measurements (e.g., measured by dynamic light scattering (DLS) or gel permeation chromatography)(8,9) typically include a bound solvated layer over the magnetic solid core material The most similar metric to that obtained magnetically is the diameter of the solid particle core obtained by transmission electron photomicrography (TEM) or scanning electron micrography (SEM). Transmission electron photomicrographs were obtained for the as-received Ferrotec EMG-607 suspension as shown in FIG. 9. Based on the measurement of the dimensions of ninety-four (94) particles from three TEM photographs, it was calculated that the Ferrotec suspension has a number average solid particle diameter of 10.3 nm, a volume average solid particle diameter of 12.75 nm, and a corresponding diameter dispersitivity of 1.24. The TEM determined number average particle diameter is 1.3 nm larger than the average value of 9.0 nm for the magnetically obtained number average particle diameters for runs MT-3 LF and MT-4 LF. This difference would be expected if the surface atoms of the magnetic particles were demagnetized due to their interaction with the surfactant molecules present in the stabilizing film that provides colloidal stability.

The volume average particle diameter obtained from the optical measurement is only 12.5 nm or 5 nm smaller than the magnetically obtained value of 17.5 nm. There is a corresponding significant difference in diameter dispersitivities, 1.24 for the TEM measurement versus 1.92±0.04 for the magnetic measurements. This difference is believed to be a result of the size of the particle populations measured. In the TEM measurements, the results presented are based on measurements performed on a miniscule sample of 94 particles. In contrast, the magnetic measurements are based on the total population of magnetic particles in the samples, which ranged from about $10^{14}$ particles for the infused chicken livers to well over $10^{15}$ particles for the concentrated ferrofluids. Because the magnetic measurements are performed on the total particle populations being evaluated, they are able to capture variations which were absent from the TEM measurements because of the very small size of the sample being evaluated. The advantages of the VSM particle measurement approach over the TEM approach go well beyond the elimination of sampling errors, in that the VSM particle measurements are made in the environment that the particles exist, and do not require the expensive routine needed to prepare the samples for their examination in vacuum.

What is claimed is:

1. A method of analyzing a tumor in a subject, the method comprising:
   sequentially introducing a plurality of solutions, each containing a predetermined range of sizes of magnetic nanoparticles (MNPs), respectively, into the tumor;
   capturing an MRI image of the tumor after the introduction of each solution;
   comparing the plurality of captured MRI images to a plurality of stored images, each stored image having corresponding MNP size and size distribution information as determined by a computer-implemented method of determining a size and size distribution of superparamagnetic nanoparticle cores in a sample comprising:
      performing a magnetic measurement analysis of the sample and generating magnetization data therefrom;
      determining an asymptotic portion of high field data from the magnetization data for each of four branches (A,B,C,D) as $M_H$ vs. 1/H where $M_H$ is the measured magnetization in a magnetic field of intensity H approaching its saturation value;
      performing a linear regression analysis of the data in each branch and generating a first correlation curve of the form $M_H=\alpha/H+\beta$;
      calculating both a number average particle volume, $\tilde{V}_n$, and a saturation magnetization, $M_{sat}$, of the sample, as a function of the first correlation curve;
      combining low field, linear data of $M_H$ for branches A and C, and branches B and D, and obtaining two plots of $M_H$ vs. H for values of H within a range from −50 Oe to +50 Oe;
      performing a linear regression analysis of the data in each branch combination and generating a second correlation curve of the form $M_H=\gamma H+\delta$;
      calculating a volume average particle volume $\tilde{V}_v$ as a function of the saturation magnetization value $M_{sat}$ obtained from the high field measurements, and using the value of the slope γ for the ratio of $M_H/H$;
      calculating a volume average spherical equivalent magnetic particle diameter $\check{D}_v$ and a number average spherical equivalent magnetic particle diameter $\check{D}_n$ as a function of $\tilde{V}_v$ and $\tilde{V}_n$; and
      calculating a dispersity value, $Đ_{d_v}$ of the sample, as a function of the diameter values $\check{D}_v$ and $\check{D}_n$; and
   analyzing the tumor as a function of the comparison of the plurality of captured MRI images to the plurality of stored images.

2. The method of claim 1, wherein:
   $Đ=(\check{D}_v/\check{D}_n)^{0.33}$.

3. The method of claim 1, wherein performing the magnetic measurement analysis of the sample and generating magnetization data therefrom comprises signal averaging to increase measurement accuracy, sensitivity and repeatability.

4. The method of claim 1, wherein performing the magnetic measurement analysis of the sample and generating magnetization data therefrom comprises:
   extracting the magnetic signals of the sample from background signals.

5. The method of claim 4, wherein extracting the magnetic signals of the sample from background signals comprises subtracting at least one of the following from the background signals:
   a magnetic profile of the sample container;
   a magnetic profile of a liquid in the sample; and
   a magnetic profile of any material in the system contributing a non-essential magnetization profile.

6. The method of claim 4, further comprising:

minimizing background signal noise by at least one of:
- cooling a pick-up coil to eliminate Johnson (thermal) noise;
- filtering by applying a noise bandwidth filter;
- filtering and regulating input power to minimize stray magnetic and electrostatic signals;
- providing local conductive flooring;
- providing localized EMF zoned-screen cages with mu-metal component shielding.

7. The method of claim 4, further comprising:

placing the sample in a sample holder, wherein extracting the magnetic signals of the sample from background signals comprises:
- determining a magnetic profile of the sample holder; and
- subtracting the sample holder magnetic profile from the background signals.

8. The method of claim 1, wherein:
1) branch A comprises magnetization data for increasing values of H from 0 Oe to +20,000 Oe;
2) branch B comprises magnetization data for decreasing values of H from +20,000 Oe to 0 Oe;
3) branch C comprises magnetization data for decreasing values of H from 0 Oe to −20,000 Oe; and
4) branch D comprises magnetization data for increasing values of H from −20,000 Oe to 0 Oe.

9. The method of claim 1, wherein the sample comprises at least one of:
- a biological matrix material;
- a liquid; and
- a solid dispersion.

10. The method of claim 1, wherein the linear regression analysis is a function of at least one of:
- a minimum allowable regression coefficient; and
- a maximum allowable signal noise level.

11. The method of claim 1, further comprising:
- placing the sample in a holder;
- determining a weight of the sample; and
- determining a magnetization profile of the holder,
- wherein generating the magnetization data comprises compensating for the determined weight of the sample and the holder magnetization profile.

12. The method of claim 11, wherein the holder comprises at least one of: plastic, quartz and carbon fiber.

13. The method of claim 11, wherein the sample is contained within a matrix material, the method further comprising:
- determining a magnetization profile of the matrix material,
- wherein generating the magnetization data comprises compensating for the matrix material magnetization profile.

14. The method of claim 13, wherein the matrix material is a biological material.

15. The method of claim 1, wherein obtaining two plots of $M_H$ vs. H further comprises obtaining the plots for values of H within a range from −10 Oe to +10 Oe.

\* \* \* \* \*